(12) United States Patent
Todd

(10) Patent No.: US 7,608,039 B1
(45) Date of Patent: Oct. 27, 2009

(54) HAND-HELD SURGICAL INSTRUMENT WITH ILLUMINATED KEYPAD

(75) Inventor: Erik F. D. Todd, Redwood City, CA (US)

(73) Assignee: Stryker Corporation, Kalamazoo, MI (US)

( * ) Notice: Subject to any disclaimer, the term of this patent is extended or adjusted under 35 U.S.C. 154(b) by 222 days.

(21) Appl. No.: 11/277,676

(22) Filed: Mar. 28, 2006

Related U.S. Application Data

(62) Division of application No. 10/677,416, filed on Oct. 1, 2003, now abandoned.

(51) Int. Cl.
*A61B 1/04* (2006.01)
*H01H 9/18* (2006.01)

(52) U.S. Cl. ............... 600/112; 600/118; 200/310; 200/313; 200/314

(58) Field of Classification Search ............ 600/109, 600/118, 131, 249, 160, 112, 133; 606/1; 362/29, 23; 200/310, 313, 314
See application file for complete search history.

(56) References Cited

U.S. PATENT DOCUMENTS

| | | | |
|---|---|---|---|
| 4,293,764 A | 10/1981 | Amrhein | |
| 4,670,633 A | 6/1987 | Kaiwa et al. | |
| 4,882,581 A * | 11/1989 | Inobe et al. | 341/22 |
| 5,373,317 A | 12/1994 | Salvati et al. | |
| 5,655,826 A * | 8/1997 | Kouno et al. | 362/24 |
| 5,830,157 A | 11/1998 | Foote | |
| 5,960,942 A | 10/1999 | Thornton | |
| 6,086,228 A | 7/2000 | McGowan et al. | |
| 6,224,542 B1 * | 5/2001 | Chang et al. | 600/109 |
| 6,589,162 B2 | 7/2003 | Nakashima et al. | |
| 6,595,653 B2 | 7/2003 | Saito et al. | |
| 6,608,270 B2 * | 8/2003 | Donofrio et al. | 200/302.1 |
| 6,612,981 B2 | 9/2003 | Onishi et al. | |
| 6,618,209 B2 * | 9/2003 | Nishioka et al. | 359/676 |
| 6,639,623 B2 * | 10/2003 | Howell et al. | 348/61 |
| 6,869,397 B2 | 3/2005 | Black et al. | |
| 6,919,914 B2 * | 7/2005 | Beutter et al. | 348/65 |
| 6,936,783 B2 | 8/2005 | Kawaguchi et al. | |
| 6,945,931 B2 | 9/2005 | Ogawa | |
| 6,947,091 B1 * | 9/2005 | Widmann et al. | 348/345 |
| 6,956,561 B2 | 10/2005 | Han | |
| 2002/0184122 A1 | 12/2002 | Yamaguchi et al. | |
| 2003/0023179 A1 | 1/2003 | Mikula et al. | |
| 2003/0128537 A1 | 7/2003 | Dorundo et al. | |
| 2004/0268391 A1 | 12/2004 | Clercq et al. | |

* cited by examiner

*Primary Examiner*—John P Leubecker
(74) *Attorney, Agent, or Firm*—Blakely, Sokoloff, Taylor & Zafman LLP

(57) ABSTRACT

A hand-held endoscopic surgical instrument, such as a camera or shaver, comprises an illuminated keypad operable by a user to operate the instrument.

3 Claims, 5 Drawing Sheets

HAND-HELD SURGICAL INSTRUMENT WITH ILLUMINATED KEYPAD

This application is a divisional of U.S. patent application Ser. No. 10/677,416 of E. Todd, filed on Oct. 1, 2003, which is incorporated herein by reference and is now abandoned.

FIELD OF THE INVENTION

At least one embodiment of the present invention pertains to surgical instruments, and more particularly, to a hand-held endoscopic surgical instrument with an illuminated keypad.

BACKGROUND

Endoscopy is a field which allows the acquisition of high-quality images of internal features of a body. In the medical fields, endoscopy often eliminates the need for fully invasive surgery. A basic tool of endoscopy is an endoscopic camera system, which includes an endoscope ("scope") that is partially inserted into the body to be viewed. Some endoscopic medical procedures involve the use of a flexible scope, as in the field of gastroenterology, for example. Others, such as arthroscopy or laproscopy, involve the use of a rigid scope. The scope is normally coupled to a camera that includes electronics for acquiring video image data.

In a typical system used for medical endoscopy, the scope is coupled to a video camera. The camera is small enough and lightweight enough to be held in a person's hand. The camera includes image sensors, such as charged-coupled devices (CCDs) or complementary metal oxide semiconductor (CMOS) image sensors, for acquiring color video image data of internal features of the body, through a system of lenses within the scope. The camera also includes a keypad or other controls to control various functions, such as focus, zoom, etc. Light is provided to the scope by a high-intensity light source through a light conduit, such as fiber optic cable. The camera is coupled to, and conveys video image data to, a camera control unit by a transmission line, such as an electrical cable. Resulting images are displayed on a video monitor.

During an endoscopic medical procedure, the operating room is typically darkened to make it easier to view the images displayed on monitors. As a result, the keypad function indicators on the camera and on other instruments, such as shaver handpieces, can be difficult to read. These functions are critical to the proper operation of the instruments.

To date, this problem has been addressed by extensive training to have the physician memorize the functionality of the keypad as it relates to the instrument. Once the lights are dimmed, the physician operates the keypad from memory. Having to memorize the keypad functionality is inconvenient and burdensome, however. Also, in the event the physician forgets certain keypad functions, it becomes necessary to turn the operating room lights back on to review the functionality of the keypad, which delays the procedure.

SUMMARY OF THE INVENTION

The present invention includes a hand-held endoscopic surgical instrument that comprises circuitry to control a function of the instrument, a control operable by a user to operate the circuitry, and a light source to illuminate the control.

Other aspects of the invention will be apparent from the accompanying figures and from the detailed description which follows.

BRIEF DESCRIPTION OF THE DRAWINGS

One or more embodiments of the present invention are illustrated by way of example and not limitation in the figures of the accompanying drawings, in which like references indicate similar elements and in which.

DETAILED DESCRIPTION

A hand-held endoscopic surgical instrument with an illuminated keypad is described. Illuminating the keypad eliminates the need for the physician to memorize the keypad functions and allows the physician to ensure he is causing the desired functions without trial and error. Illuminating the keypad also reduces the likelihood of having to delay the procedure in order to turn the operating room lights on and review the functionality of the keypad.

Figure 1:
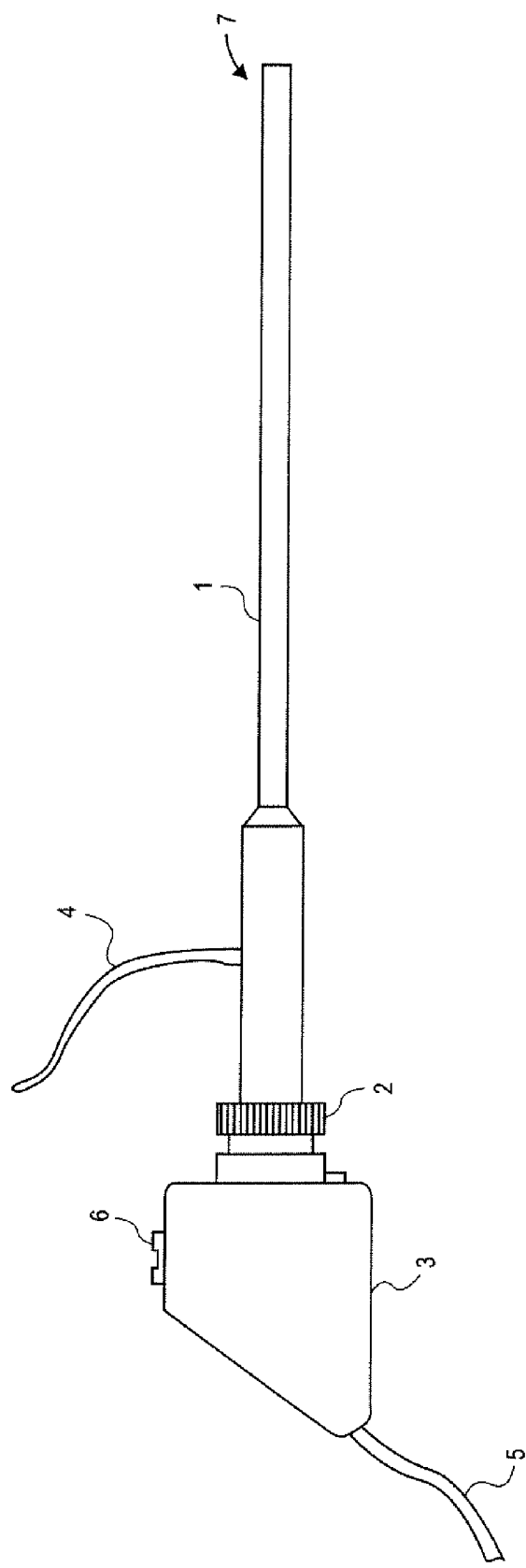
FIG. 1 illustrates a portion of an endoscopic imaging system including an endoscopic camera coupled to a scope.

FIG. 1 illustrates a portion of an endoscopic camera system. The illustrated components include a rigid scope 1 of the type commonly used for laproscopy or arthroscopy. The scope 1 is coupled to a camera 3 by a coupler 2. During endoscopic surgery, the distal end 7 of the scope 1 is inserted into the body of the patient through a very small incision. Light is provided to the scope 1 by a high-intensity light source (not shown) through a light conduit 4, such as fiber optic cable.

The camera 3 is coupled to, and conveys video image data to, a camera control unit (not shown) by a transmission line 5, such as an electrical cable. Resulting images are displayed on a video monitor (not shown). The camera 3 is small enough and lightweight enough to be held in a person's hand. Inside the camera 3 are (among other things) image sensors, such as charged-coupled devices (CCDs) or complementary metal oxide semiconductor (CMOS) image sensors, for acquiring color video image data of internal features of the body, through a system of lenses within the scope 1. The camera 3 includes a set of controls 6, such as a keypad including a number of keys, which can be operated by a user to electronically control various functions of the camera, such as focus, zoom, brightness, contrast, etc.

Figure 2:
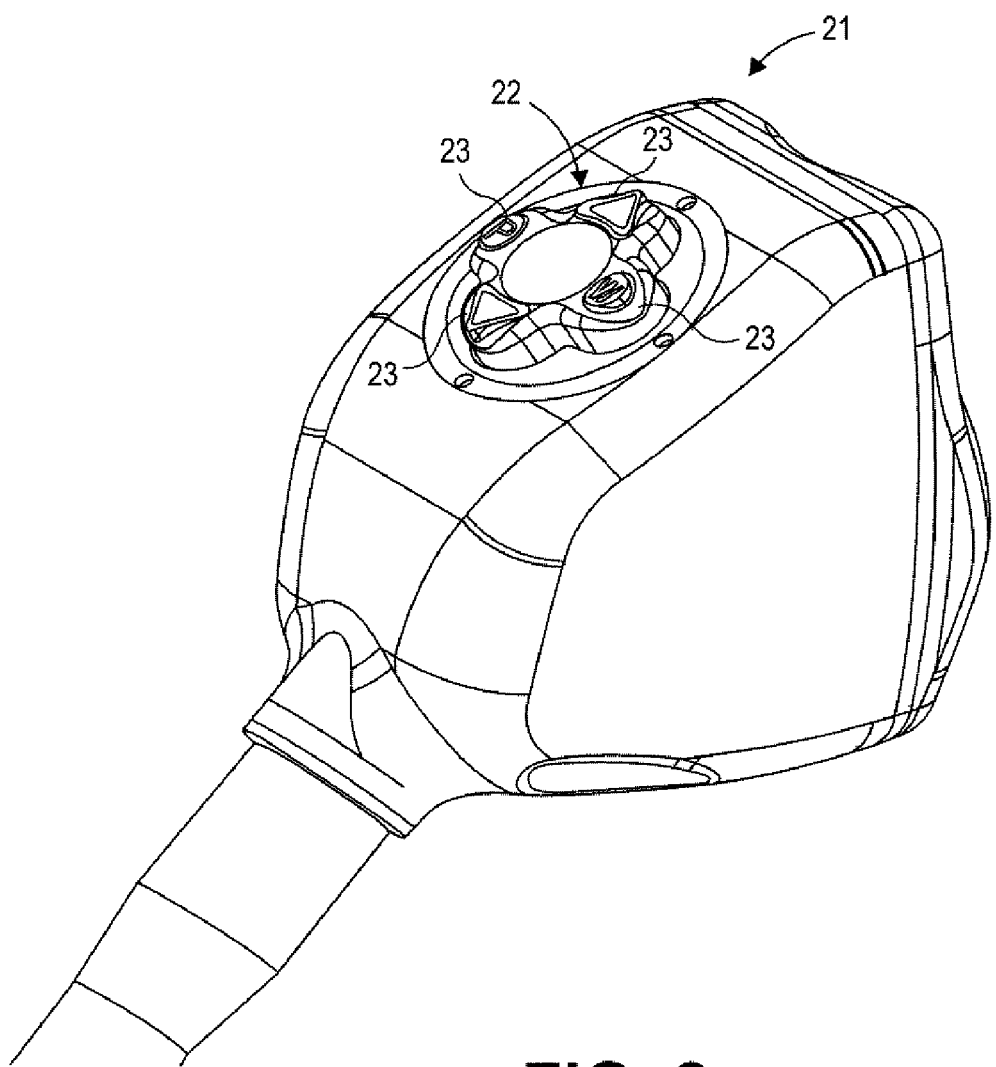
FIG. 2 illustrates an endoscopic camera with a keypad.

FIG. 2 shows a perspective view of another embodiment of an endoscopic video camera 21, which also includes a keypad 22 to control functions of the camera. The keypad 22 in this embodiment includes four keys 23. The function of each key 23 is indicated by a function indicator (e.g., symbols or text) on the top of each key, which in the illustrated example are up and down arrows and the letters "P" and "W". The function assigned to any key 23 is activated by the user of the camera pressing the key 23. The keypad 22 can be made of a single piece of pliable material, such as injection-molded silicone or any other material suitable for this purpose (such as may be used to make the keypads of remote controls for various commonly-available consumer electronic devices). Alternatively, the keypad 22 can be formed from separate pieces of such a material, e.g., to form separate keys 23.

In accordance with the invention, a light source is added to the camera 21 to illuminate the keypad 22. In one embodiment of the invention, the light source is a phosphorescent substance, such as PermaGlow luminescent powder from Hirotec Inc. of Huntington Beach, Calif., which is mixed with the material of the keypad 22 during molding of the keypad 22, so as to make the keypad 22 self-illuminating. In such an embodiment, the function indicators may be opaque symbols printed or painted on the top surface of the keys 23, such that the glowing of the rest of the keypad 22 makes the function indicators more visible in a dark environment. In another embodiment, the phosphorescent substance may be applied to the surface of the keypad 22. In that case, the keypad 22 may be made to glow except for the function indicators which are made non-glowing; or, only the function indicators may be made to glow, while the rest of the keypad 22 is made non-glowing.

In another embodiment, the keypad 22 is illuminated through the use of a light source separate from the keypad, such as one or more light-emitting diodes (LEDs) that can emit very strong light rays with minimal energy requirements. The LED may be installed under the translucent keypad 22, and the function indicators may be opaque symbols printed or painted on the top surface of the keys 23, such that the light shining through the keypad 22 makes the function indicators more visible in a dark environment.

Figure 3:
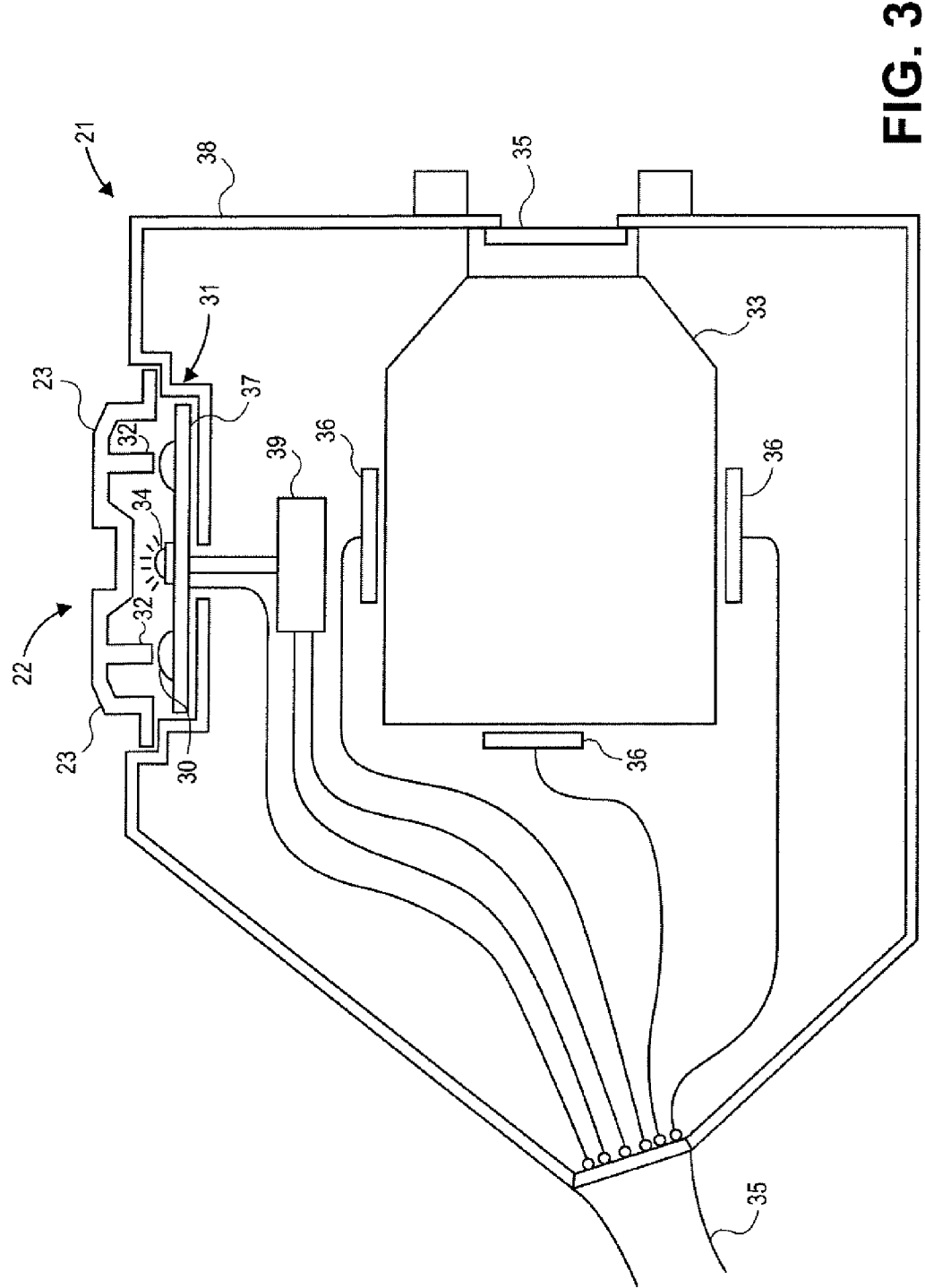
FIG. 3 schematically shows a quasi-cross-sectional side view of an endoscopic camera which includes an LED to illuminate the keypad.

FIG. 3 schematically shows a quasi-cross-sectional side view of the camera 21, according to an embodiment which uses an LED to illuminate the keypad 22. The camera 21 includes a number of image sensors 36 and a light guide 33. The light guide 33 may include one or more prisms optically coupled to the aperture window 35 and to the image sensors 36. The image sensors 36 may be, for example, CCDs, CMOS sensors, or the like. For example, there may be three image sensors 36, one each for the red, green, and blue color components of a conventional video signal. The image sensors 36 are electrically connected to external transmission line 35, the other end of which terminates at a camera control unit (CCU) (not shown).

The upper portion of the housing 38 of the camera 21 has a recessed region 31, in which the keypad 22 is mounted. The keypad 22 is positioned so that its upper portion extends above the top surface of the housing 38 and its lower portion extends into the recessed portion 31.

The keypad 22 is mounted on top of a switch assembly which includes a circuit board 37 or other suitable element with a set of flexible dome switches mounted thereon. When a key 23 is pressed down by a user, a peg 32 formed on the bottom side of the key 23 pushes downward on a contact 30 of the corresponding dome switch. This action causes a circuit to be completed, thereby causing the desired function.

Also mounted on the circuit board 37 underneath the keypad 22 is an LED 34 (or multiple LEDs) or other similar light source(s), which illuminates the keypad 22 when the camera 21 is operating.

Some of the switch contacts 30 may be coupled, through appropriate terminals on the circuit board 37, to additional circuitry 39 inside the camera 21, which causes the desired function. Others of the switch contacts 30 may be coupled, through appropriate terminals on the circuit board 37 and wiring within the camera 21, to the camera control unit (not shown) via the external transmission line 35. In the latter case, the camera control unit receives the signal, handles the signal in an appropriate manner, and then returns a return signal through the transmission line 35, where it is acted upon accordingly by the camera 21.

Figure 4:
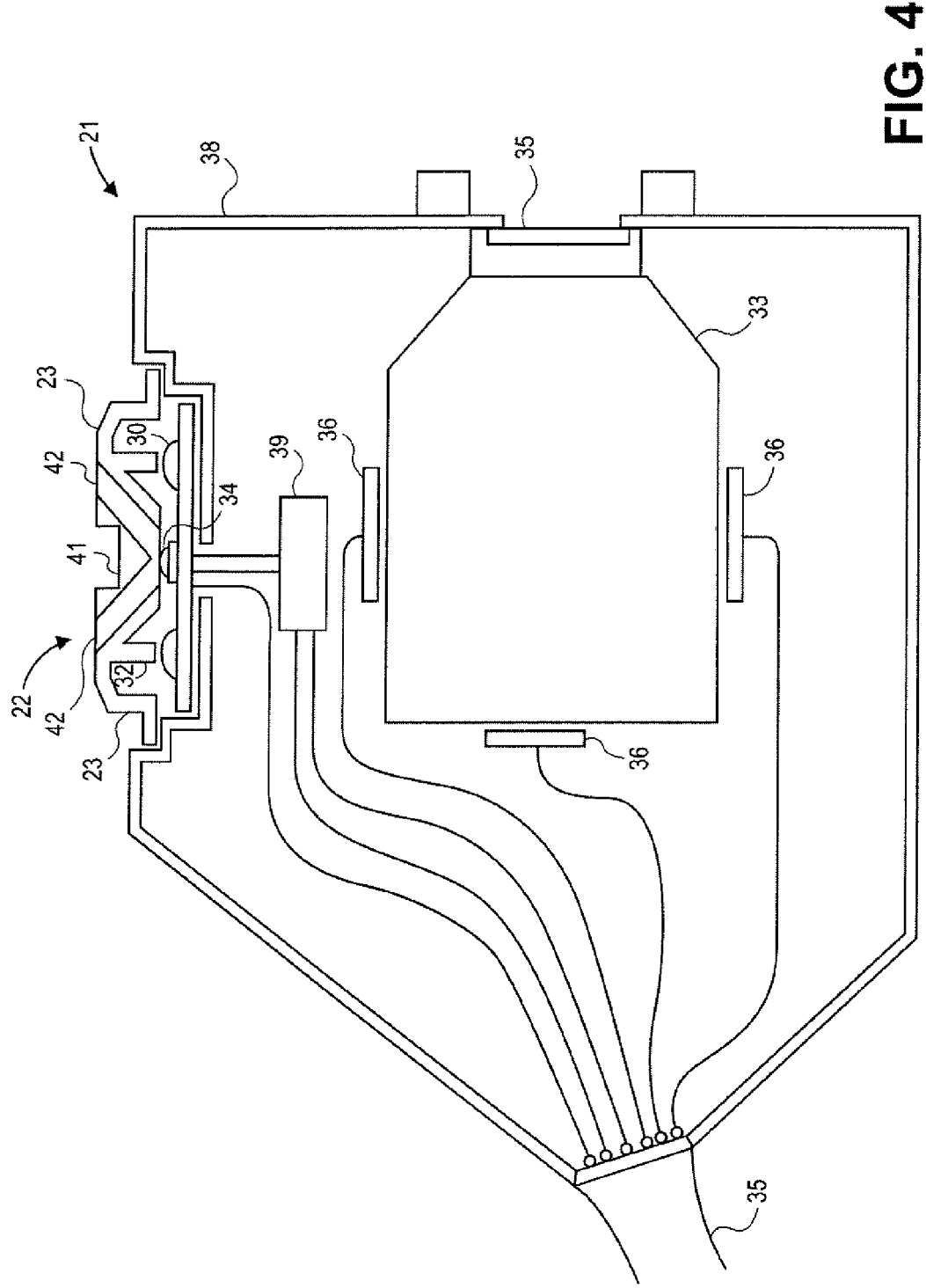
FIG. 4 shows a view similar to FIG. 3 but for an embodiment that includes a light pipe to channel light from the LED to the keypad.

Another embodiment of the invention is illustrated in FIG. 4. This embodiment is substantially similar to that of FIG. 3, except that the keypad 22 is illuminated through the use of a light pipe 41. The light pipe 41 may be integral with (embedded in) the keypad 22, as shown in FIG. 4, which may be created using a "two-shot" mold process. Alternatively, the light pipe 41 may be a separate piece from the keypad 22. In an embodiment which uses the light pipe 41, most of the keypad 22 is opaque, except for the function indicators which are clear or translucent. The light pipe 41 channels light from the LED 34 to each of the function indicators. The functions indicators may be formed from the upper ends 42 of the light pipe 41, which are molded in the form of symbols. The light pipe 41 may be formed from substantially clear plastic or other material suitable for channeling light in this manner.

Figure 5:
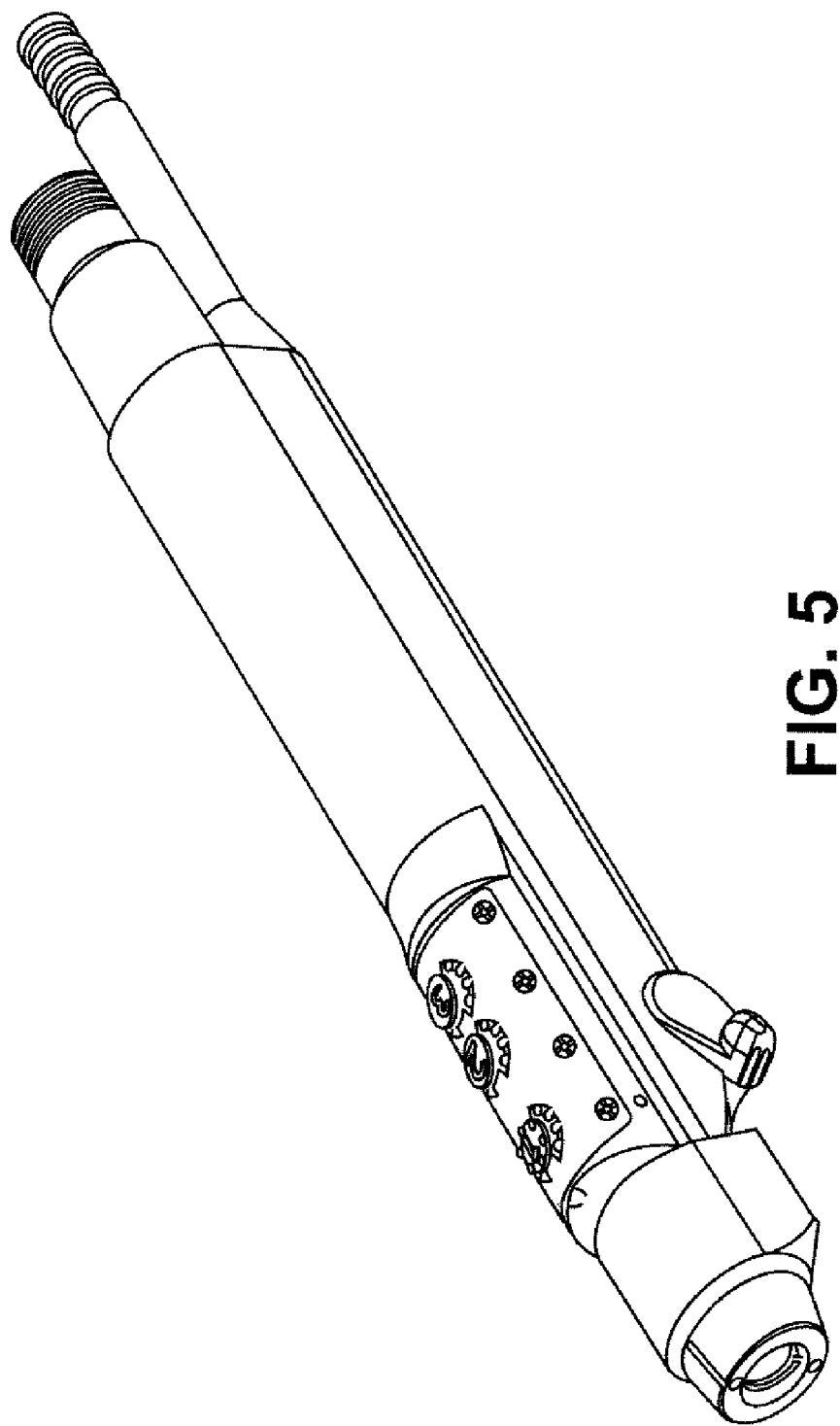
FIG. 5 illustrates a shaver handpiece with a keypad.

Note that the above-described techniques are not limited to use in endoscopic cameras. These techniques can also be applied to provide illuminated controls in various other types of hand-held surgical instruments and other devices. As just one example, these techniques can be used to provide an illuminated keypad on a hand-held shaver handpiece used for endoscopic surgery, an example of which is shown in FIG. 5. Numerous other applications are conceivable.

Thus, a hand-held endoscopic surgical instrument with an illuminated keypad has been described. Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. An apparatus comprising:
   a hand-held endoscopic surgical camera including
      a housing for the endoscopic camera, wherein an upper portion of the housing slopes downward towards a user of the endoscopic camera and includes a recessed region;
      circuitry, within the housing, to control functionality of the hand-held endoscopic surgical camera, wherein the endoscopic surgical camera includes focus and zoom functions;
      a control operable by a user to operate the circuitry, wherein the control includes a keypad made of a single piece of pliable material and including four keys mounted in a cross-like configuration, wherein the keypad electronically controls the focus and zoom functions of the endoscopic surgical camera and wherein the keypad is mounted so that a upper portion of the keypad extends above the upper portion of the housing and a lower portion of the keypad extends into the recessed region; and
      a light source to illuminate the control, wherein the light source is a phosphorescent substance that is integral with the keypad, and wherein the keypad includes opaque symbols that are not self-illuminating on the top surface of the keypad to indicate corresponding functions, such that the control is self-illuminating and the opaque symbols are visible in a dark environment in contrast to the rest of the self-illuminating keypad.

2. The apparatus as recited in claim 1, wherein the phosphorescent substance is integrated within the pliable material of which the control is formed.

3. The apparatus as recited in claim 2, wherein the pliable material of which the control is formed comprises silicone.

* * * * *